(12) United States Patent
Huiku

(10) Patent No.: US 8,694,067 B2
(45) Date of Patent: Apr. 8, 2014

(54) SENSOR, APPARATUS AND METHOD FOR NON-INVASIVELY MONITORING BLOOD CHARACTERISTICS OF A SUBJECT

(75) Inventor: Matti Huiku, Espoo (FI)

(73) Assignee: General Electric Company, Schenectady, NY (US)

(*) Notice: Subject to any disclaimer, the term of this patent is extended or adjusted under 35 U.S.C. 154(b) by 510 days.

(21) Appl. No.: 13/027,544

(22) Filed: Feb. 15, 2011

(65) Prior Publication Data
US 2012/0209095 A1    Aug. 16, 2012

(51) Int. Cl.
*A61B 5/1455* (2006.01)

(52) U.S. Cl.
USPC ............................ 600/322; 600/310; 600/323

(58) Field of Classification Search
USPC .................................................. 600/309–344
See application file for complete search history.

(56) References Cited

U.S. PATENT DOCUMENTS

| | | |
|---|---|---|
| 5,297,548 A | 3/1994 | Pologe |
| 5,321,265 A * | 6/1994 | Block ........................ 250/343 |
| 5,902,235 A | 5/1999 | Lewis et al. |
| 6,553,242 B1 * | 4/2003 | Sarussi ........................ 600/330 |
| 6,741,875 B1 * | 5/2004 | Pawluczyk et al. ........... 600/310 |
| 2010/0041970 A1 * | 2/2010 | Hedberg et al. ............... 600/333 |

* cited by examiner

*Primary Examiner* — Eric Winakur
*Assistant Examiner* — Marjan Fardanesh
(74) *Attorney, Agent, or Firm* — Andrus Intellectual Property Law, LLP

(57) ABSTRACT

A sensor, apparatus and method for non-invasively monitoring blood characteristics of a subject are disclosed. The sensor comprises an emitter unit configured to emit radiation through the tissue of the subject at a plurality of measurement wavelengths and a detector unit that comprises photo detectors. To achieve a simple sensor assembly, the photo detectors are together adapted to receive the radiation at the plurality of wavelengths and to produce in-vivo measurement signals corresponding to the plurality of measurement wavelengths, the in-vivo measurement signals being indicative of absorption caused by blood of the subject. Furthermore, the photo detectors are mounted so that optical paths from the emitter unit to the photo detectors are different, and the plurality of wavelengths are divided between the photo detectors so that two spectrally adjacent photo detectors have at least one common wavelength. The apparatus comprises a path normalization unit configured to normalize the in-vivo measurement signals to an optical path specific to one of the photo detectors.

11 Claims, 3 Drawing Sheets

SENSOR, APPARATUS AND METHOD FOR NON-INVASIVELY MONITORING BLOOD CHARACTERISTICS OF A SUBJECT

BACKGROUND OF THE INVENTION

This disclosure relates to a sensor, apparatus and method for non-invasively monitoring blood characteristics of a subject. The apparatus is typically a pulse oximeter, while the sensor is typically a pulse oximeter sensor attachable to a subject and adapted to acquire (photo) plethysmographic signals from the subject.

Plethysmography refers to measurement of changes in the sizes and volumes of organs and extremities by measuring changes in blood volume. Photoplethysmography relates to the use of optical signals transmitted through or reflected by blood for monitoring a physiological parameter of a subject. Conventional pulse oximeters use red and infrared photoplethysmographic (PPG) waveforms, i.e. waveforms measured respectively at red and infrared wavelengths, to determine oxygen saturation of pulsatile arterial blood of a subject. The two wavelengths used in a conventional pulse oximeter are typically around 660 nm (red wavelength) and 940 nm (infrared wavelength).

Pulse oximetry is at present the standard of care for continuous monitoring of arterial oxygen saturation ($SpO_2$). Pulse oximeters provide instantaneous in-vivo measurements of arterial oxygenation, and thereby an early warning of arterial hypoxemia, for example. Pulse oximeters also display the photoplethysmographic waveform, which can be related to tissue blood volume and blood flow, i.e. the blood circulation, at the site of the measurement, typically in finger or ear.

Traditionally, pulse oximeters use the above-mentioned two wavelengths, red and infrared, to determine the oxygen saturation. Other parameters that may be determined in a two-wavelength pulse oximeter include pulse rate, peripheral perfusion index (PI) and pleth variability index (PVI), for example. Increasing the number of wavelengths to at least four allows the measurement of total hemoglobin (THb, grams per liter) and different hemoglobin types, such as oxyhemoglobin ($HbO_2$), deoxyhemoglobin (RHb), carboxyhemoglobin (HbCO), and methemoglobin (metHb). A prerequisite of the measurement of total hemoglobin is that the wavelengths used extend up to a range where water absorption is high, thereby to be able to detect the concentrations of both hemoglobin and water. In practice, a pulse oximeter designed to measure total hemoglobin may be provided with 8 to 16 wavelengths (i.e. light sources) ranging from around 600 nm up to around 1300 nm.

The measurement of the blood characteristics is typically predicated on the assumption that the light beams from the different light sources follow identical paths through the intervening tissue to the photo detector. If this assumption is not made, the measurement becomes very complicated as the path lengths need to be determined for each wavelength. However, in multi-wavelength oximeters capable of determining total hemoglobin the use of multiple photo detectors becomes a necessity since there is no photo detector available that is capable of receiving such a wide range of wavelengths with acceptable reception characteristics. For example, the responsivity of widely used silicon photo detectors drops rather abruptly around 1000 nm, while modern InGaAs (indium gallium arsenide) photo detectors are sensitive from approximately 900 nm to approximately 1700 nm.

Consequently, the sensor of a multi-wavelength pulse oximeter is normally designed so that the light beams travel substantially along a common path through the tissue to be monitored, i.e. that the optical path length through the arteriolar bed is substantially the same for all wavelengths. As to the transmission end of the optical signals, it is normally not difficult to arrange the multiple small size light sources of the sensor in a substantially point-like fashion so that the optical path remains substantially the same for all wavelengths at the transmission end. However, it is more difficult to arrange two photo detectors, which have a rather large area, within the sensor so that the same requirement is fulfilled also at the reception end, thereby to avoid introduction of error into the measurement due to the inability of the sensor to transmit the light pulses along a common path at all wavelengths.

One solution for the above problem is to use a sandwich or layered detector design in the sensor. This involves that the photo detector consists of a multiple layer detector element that comprises two detector layers placed on top of each other. For example, a germanium photodiode may be placed under a silicon photodiode. This layered element operates so that for wavelengths under about 1000 nm the upper silicon photodiode receives the transmitted light. Above this wavelength, the silicon photodiode becomes substantially transparent and the lower germanium photodiode receives the light pulses.

A drawback of the sandwich or layered detector design is the rather complex mechanical structure that requires accuracy in the manufacturing process. These properties tend to translate into high costs for the end user, which in turn hampers the introduction and proliferation of the multi-wavelength measurements. In the sandwich design, the top detector also attenuates the light received by the bottom detector, which thus typically has a lower sensitivity than the detector exposed to direct light beams.

BRIEF DESCRIPTION OF THE INVENTION

The above-mentioned problems are addressed herein which will be comprehended from the following specification.

To achieve a simple sensor assembly, photo detectors having partly overlapping spectral responsivity ranges are mounted in the sensor without making the optical paths to the detectors the same. At least one of the wavelengths of the sensor is set to emit in the overlapping range, thereby to enable normalization of the plethysmographic signals with respect to the optical paths. This path normalization is an operation that converts the plethysmographic signals as if the signals were received through a single photo detector, i.e. the signals are adapted to a single path length norm or reference. Therefore, the mechanical structure of the sensor is not required to implement a common optical path and the detectors may be mounted in a simple manner within the sensor, such as side by side.

In an embodiment, a sensor for determining blood characteristics of a subject comprises an emitter unit configured to emit radiation through the tissue of the subject at a plurality of measurement wavelengths. The sensor further includes a detector unit comprising photo detectors that are together adapted to receive the radiation at the plurality of wavelengths and to produce in-vivo measurement signals corresponding to the plurality of measurement wavelengths, the in-vivo measurement signals being indicative of absorption caused by blood of the subject, wherein the photo detectors are mounted so that optical paths from the emitter unit to the photo detectors are different and wherein the plurality of wavelengths are divided between the photo detectors so that two spectrally adjacent photo detectors have at least one common wavelength.

In another embodiment, an apparatus for determining blood characteristics of a subject comprises an interface unit configured to receive in-vivo measurement signals from photo detectors, wherein the in-vivo measurement signals are indicative of absorption caused by blood of a subject and wherein each photo detector is adapted to receive optical signals from an optical path specific to the detector. The apparatus further comprises a path normalization unit configured to normalize the in-vivo measurement signals to an optical path specific to one of the photo detectors.

In yet another embodiment, a method for determining blood characteristics of a subject comprises mounting multiple photo detectors in a sensor arrangement so that optical paths from an emitter unit to the photo detectors are different and providing the emitter unit with a plurality of measurement wavelengths. The method also includes acquiring in-vivo measurement signals at the plurality of measurement wavelengths, the in-vivo measurement signals being indicative of absorption caused by blood of a subject and determining a path normalization coefficient based on different in-vivo measurement signals obtained respectively from different photo detectors at a wavelength common to the different photo detectors. The method further comprises applying the path normalization coefficient to selected in-vivo measurement signals, thereby to obtain path normalized in-vivo measurement signals and employing the path normalized in-vivo measurement signals for determining blood characteristics of the subject.

Various other features, objects, and advantages of the invention will be made apparent to those skilled in the art from the following detailed description and accompanying drawings.

DETAILED DESCRIPTION OF THE INVENTION

A pulse oximeter comprises a computerized measuring unit and a sensor or probe attached to the patient, typically to finger or ear lobe of the patient. The sensor includes a light source for sending an optical signal through the tissue and a photo detector for receiving the signal transmitted through or reflected from the tissue. On the basis of the transmitted and received signals, light absorption by the tissue may be determined. During each cardiac cycle, light absorption by the tissue varies cyclically. During the diastolic phase, absorption is caused by venous blood, non-pulsating arterial blood, cells and fluids in tissue, bone, and pigments, whereas during the systolic phase there is an increase in absorption, which is caused by the inflow of arterial blood into the tissue part on which the sensor of the pulse oximeter is attached. Pulse oximeters focus the measurement on this pulsating arterial blood portion by determining the difference between the peak absorption during the systolic phase and the background absorption during the diastolic phase. Pulse oximetry is thus based on the assumption that the pulsatile component of the absorption is due to arterial blood only In order to distinguish between two species of hemoglobin, oxyhemoglobin ($HbO_2$), and deoxyhemoglobin (RHb), absorption must be measured at two different wavelengths, i.e. the sensor of a traditional pulse oximeter includes two different light sources, such as LEDs or lasers. The wavelength values widely used are 660 nm (red) and 940 nm (infrared), since the said two species of hemoglobin have substantially different absorption at these wavelengths. Each light source is illuminated in turn at a frequency which is typically several hundred Hz.

Figure 1:
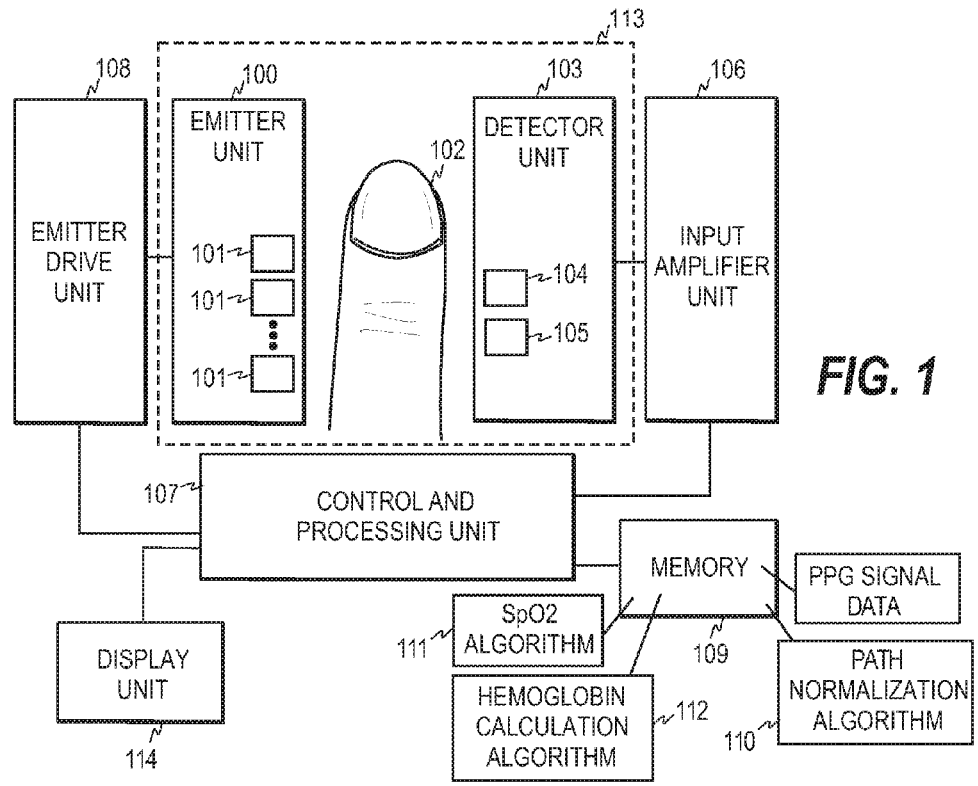
FIG. 1 is a block diagram illustrating one embodiment of a multi-wavelength pulse oximeter.

FIG. 1 is a block diagram of one embodiment of a multi-wavelength pulse oximeter. Light transmitted from an emitter unit 100 passes into patient tissue, such as a finger 102. The emitter unit includes multiple light sources 101, such as LEDs, each light source having a dedicated wavelength. Each wavelength forms one measurement channel on which photoplethysmographic waveform data is acquired. The number of sources/wavelengths is at least three and typically between 8 and 16. Below, an example is given in which eight wavelengths are used.

The light propagated through or reflected from the tissue is received by a detector unit 103, which comprises two photo detectors 104 and 105 in this example. The emitter and detector units form the sensor 113 of the pulse oximeter.

The photo detectors convert the optical signals received into electrical pulse trains and feed them to an input amplifier unit 106. The amplified measurement channel signals are further supplied to a control and processing unit 107, which converts the signals into digitized format for each wavelength channel. The measurement channels are divided between the photo detectors so that each measurement channel has a dedicated photo detector operating as an optical receiver. Furthermore, both photo detectors are adapted to receive the signals of at least one of the measurement channels, i.e. at least one wavelength is common to the photo detectors.

The control and processing unit further controls an emitter drive unit 108 to alternately activate the light sources. As mentioned above, each light source is typically illuminated several hundred times per second. With each light source being illuminated at such a high rate compared to the pulse rate of the patient, the control and processing unit obtains a high number of samples at each wavelength for each cardiac cycle of the patient. The value of these samples varies according to the cardiac cycle of the patient, the variation being caused by the arterial blood.

The digitized photoplethysmographic (PPG) signal data at each wavelength may be stored in a memory 109 of the control and processing unit before being processed further by the algorithms of the control and processing unit. These algorithms utilize plethysmographic signal data that is normalized with respect to the optical paths of the sensor. The control and processing unit derives the path normalized signal data by executing a path normalization algorithm 110.

For the determination of oxygen saturation and hemoglobin parameters the control and processing unit is adapted to execute an $SpO_2$ algorithm 111 and a hemoglobin algorithm 112, which may also be stored in the memory of the control and processing unit. Both algorithms may utilize the same digitized signal data or the hemoglobin algorithm may utilize the results derived in the $SpO_2$ algorithm. The path normalization algorithm 110 may also be integrated into the $SpO_2$ and/or hemoglobin algorithms. The obtained blood parameters and waveforms are shown on the screen of a display unit 114.

Figure 2:
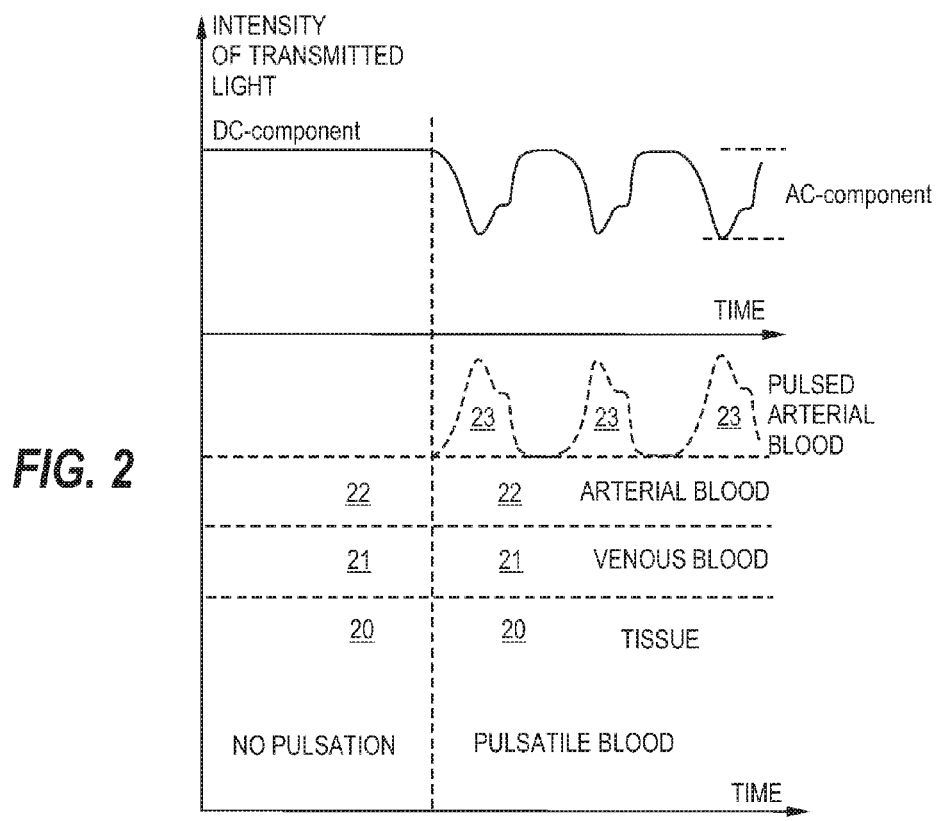
FIG. 2 illustrates a simple model based on the Lambert-Beer theory of pulse oximetry.

FIG. 2 illustrates the Lambert-Beer tissue model and how the intensity of light transmitted through a finger, for example, varies according to blood pulsation. The Lambert-Beer theory is based on a multilayer model in which light absorption is caused by different tissue compartments or layers stacked on each other. As illustrated in the figure, the tissue compartments include the actual tissue layer 20, layers of venous and arterial blood, 21 and 22, and the layer of pulsed arterial blood 23. The model assumes that the layers do not interact with each other and that each layer obeys the ideal Lambert-Beer model, in which light scattering is omitted. The ideal signal measured by a pulse oximeter in the Lambert-Beer model is thus the signal that is left when the absorption caused by each layer is deducted from the input light signal. The total absorption may thus be regarded as the total absorption caused by the actual tissue, venous blood, arterial blood, and pulsed arterial blood.

In order for variations in extrinsic factors, such as the brightness of the light sources, sensitivity of the detector, or thickness of the finger, to have no effect on the measurement, each signal received is normalized by extracting the AC component oscillating at the cardiac rhythm of the patient, and then dividing the AC component by the DC component of the light transmission or reflection. The signal thus obtained is independent of the above-mentioned extrinsic factors. Thus, the control and processing unit 107 utilizes N normalized signals, which are in this context denoted with $$dAi = \frac{ACi}{DCi},$$

where i is the wavelength in question (i=1, ... N), ACi is the AC component at wavelength i and DCi is the DC component at wavelength i. The AC and DC components are illustrated in FIG. 2. Although signals dAi are intensity normalized signals, they are not referred to as normalized signals in this context but as modulation signals, in order to distinguish them from path normalized signals derived from the modulation signals.

Figure 3:
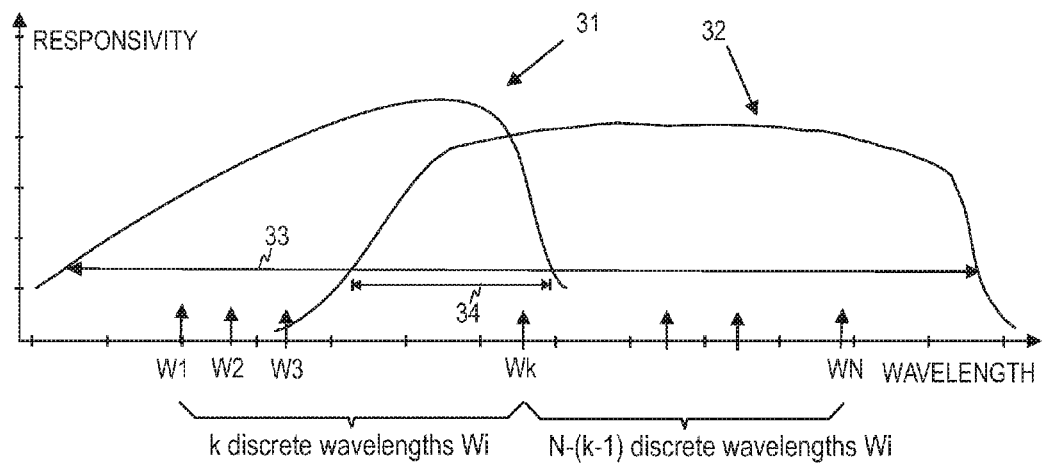
FIG. 3 illustrates an example of the spectral responsivities of the photo detectors and an example of the allocation of the sensor wavelengths to the detectors.

FIG. 3 illustrates an example of the responsivity curves of the photo detectors 104, 105 and the arrangement of the wavelengths, i.e. the measurement channels, with respect to the responsivity curves. Photo detector 104, which may be a Si (silicon) photodiode, for example, has a responsivity curve 31, while photo detector 105, which may be an InGaAs (indium gallium arsenide) photodiode, for example, has a responsivity curve 32. Together the responsivity curves cover a certain acceptable spectral sensitivity range 33 that comprises a common sensitivity range 34, where both photo detectors may receive optical signals. In case of Si and InGaAs detectors, the total sensitivity range 33 may cover wavelengths from about 400 nm to about 1700 nm and the commonly shared wavelength area 34 may range from about 800 nm to about 1000 nm, for example. The photodiodes may be PIN or PN type photodiodes.

At least one of the sensor light sources 101 is set to emit in the common wavelength range 34. This wavelength is denoted with Wk in FIG. 3. Thus, in the embodiment of FIG. 3, photo detector 104 is adapted to receive k wavelengths (W1, W2, ... , Wk, where k≥2), while photo detector 105 is adapted to receive N−(k−1) wavelengths (Wk, W(k+1) ... , WN), where N≥3 corresponds to the total number of sensor wavelengths.

Figure 4:
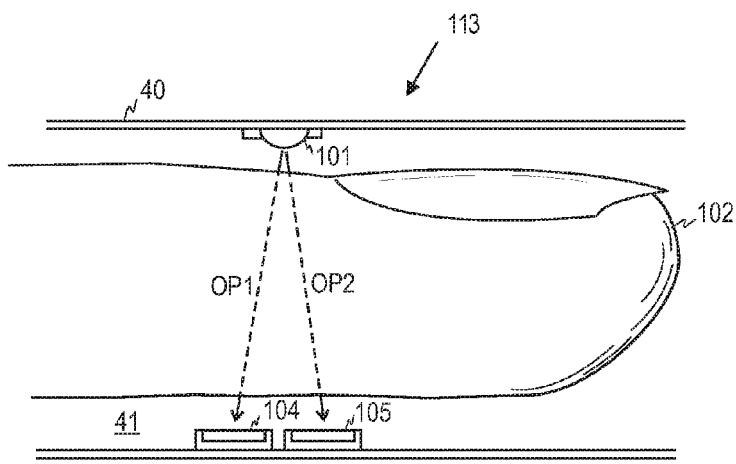
FIG. 4 illustrates a cross section view of one embodiment of a sensor.

FIG. 4 illustrates a photo detector configuration by showing a cross section view of one embodiment of the sensor 113. The frame 40 of the sensor comprises a cavity 41 into which a finger 102 may be inserted. The light sources 101 and the photo detectors 104, 105 are mounted on opposite sides of the cavity so that the light pulses emitted by the light sources travel through the finger to the photo detectors. In this embodiment, the photo detectors are mounted simply side by side on one side of the cavity. This kind of lateral juxtaposed positioning of the two photo detectors involves that the optical path OP1 from the light sources to the first photo detector 104 is not the same as the optical path OP2 from the light sources to the second photo detector 105. The different optical paths normally introduce error in the measurement but the error is now eliminated or minimized by adapting the electrical modulation signals to the same optical path, i.e. to one of the paths OP1 and OP2. The conversion is termed path normalization in this context. The path normalization is carried out in the control and processing unit, cf. algorithm 110. In the example of the figure, the photo detectors are side by side substantially in the longitudinal direction of the sensor, but may also be side by side also in any other direction. Thus, the photo detectors are mounted in the sensor so that the optical paths from the emitter unit to the photo detectors are different. This involves that the difference in the optical path lengths is so clear that it would normally introduce error in the measurement for at least some subjects. The distance between the detectors that causes significant difference to the optical path lengths through the tissue is statistical in nature and depends on the fit of the sensor, tissue thickness and inhomogeneity of tissue structures at the measurement site, for example. A certain (small) distance between the detectors may therefore cause a significant error for some subjects but not for others.

According to the Lambert-Beer model, the modulation signals dAi may be described as: $dAi = C \times (\epsilon_i^{HbO2} \times HbO2 + \epsilon_i^{RHb} \times RHb + \epsilon_i^{HbCO} \times HbCO + \epsilon_i^{HbMet} \times HbMet)$, where C is constant that depends on the path length, $\epsilon_i^{HbO2}$ is the extinction coefficient of oxyhemoglobin at wavelength i, $\epsilon_i^{RHb}$ is the extinction coefficient of deoxyhemoglobin at wavelength i, $\epsilon_i^{HbCO}$ is the extinction coefficient of carboxyhemoglobin at wavelength i, $\epsilon_i^{HbMet}$ is the extinction coefficient of methemoglobin at wavelength i, and HbO2, RHb, HbCO, and HbMet are the concentrations of oxyhemoglobin, deoxyhemoglobin, carboxyhemoglobin, and methemoglobin, respectively.

Figure 5:
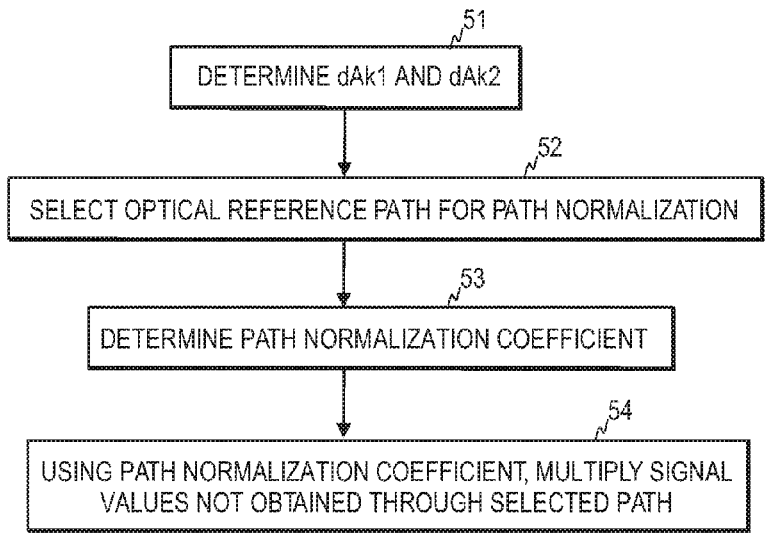
FIG. 5 is a flow diagram illustrating the path normalization of the plethysmographic signals.

FIG. 5 illustrates one embodiment of the path normalization carried out in the control and processing unit. As discussed above, the path normalization may be regarded as an adaptation of the modulation signals to a single optical path. The value of dAk is first measured at step 51 using both photo detectors, thereby to obtain dAk1 and dAk2, where dAk1 is the modulation signal at wavelength Wk measured through photo detector 104, dAk2 is the modulation signal at wavelength Wk measured through photo detector 105, and Wk is the wavelength in the common sensitivity range 34. The ratio of the two dAk values is then used to convert the modulation signals so as if all modulation signals were received from the same optical path, i.e. through the same photo detector. Since the signals may be normalized to either of the optical paths, the reference path may be selected at step 52 prior to the actual normalization. It is assumed here that the total number of wavelengths is N=8. One example of such a dual optical path length sensor is a sensor provided with wavelengths 612, 632, 660, 690, 760 and 900 nm (Si detector signals) primarily for HbCO and HbMet measurement and with wavelengths 900, 1050, and 1250 nm (InGaAs detector signals) primarily for the total hemoglobin measurement. Thus, the 900 nm wavelength is common for the detectors (i.e. here k=6). If the first optical path OP1 is selected to be the common optical reference path, the signals that are received through the second optical path OP2 need to be converted as if they were received from the first optical path. For this, the modulation signals $dA_i$ obtained from photo detector 105 are multiplied by a ratio (dAk1/dAk2). If the second optical path OP2 is selected to be the common optical reference path, the signals that are received through the first optical path OP1 need to be converted as if they were received over the second optical path. For this, the modulation signals dAi obtained from photo detector 104 are multiplied by a ratio (dAk2/dAk1). The ratio, termed path normalization coefficient here, is determined in step 53 and the actual normalization of the modulation signal values is carried out in step 54.

Thus, if the first optical path OP1 is selected to be the common optical reference path, path normalization may be presented as follows:

$$\begin{pmatrix} dA1 \\ dA2 \\ dA3 \\ dA4 \\ dA5 \\ dA6 \\ \left(\frac{dA61}{dA62}\right) \times dA7 \\ \left(\frac{dA61}{dA62}\right) \times dA8 \end{pmatrix} = C(OP1) \times \begin{pmatrix} \varepsilon_1^{HbO2} & \varepsilon_1^{RHb} & \varepsilon_1^{HbCO} & \varepsilon_1^{HbMet} \\ \varepsilon_2^{HbO2} & \varepsilon_2^{RHb} & \varepsilon_2^{HbCO} & \varepsilon_2^{HbMet} \\ \varepsilon_3^{HbO2} & \varepsilon_3^{RHb} & \varepsilon_3^{HbCO} & \varepsilon_3^{HbMet} \\ \varepsilon_4^{HbO2} & \varepsilon_4^{RHb} & \varepsilon_4^{HbCO} & \varepsilon_4^{HbMet} \\ \varepsilon_5^{HbO2} & \varepsilon_5^{RHb} & \varepsilon_5^{HbCO} & \varepsilon_5^{HbMet} \\ \varepsilon_6^{HbO2} & \varepsilon_6^{RHb} & \varepsilon_6^{HbCO} & \varepsilon_6^{HbMet} \\ \varepsilon_7^{HbO2} & \varepsilon_7^{RHb} & \varepsilon_7^{HbCO} & \varepsilon_7^{HbMet} \\ \varepsilon_8^{HbO2} & \varepsilon_8^{RHb} & \varepsilon_8^{HbCO} & \varepsilon_8^{HbMet} \end{pmatrix} \times \begin{pmatrix} HbO2 \\ RHb \\ HbCO \\ HbMet \end{pmatrix},$$

where C(OP1) is now a constant depending on optical path OP1. Thus, in this example the modulation signals at wavelengths 1050 and 1250 nm are converted as if received through photo detector 104.

Figure 6:
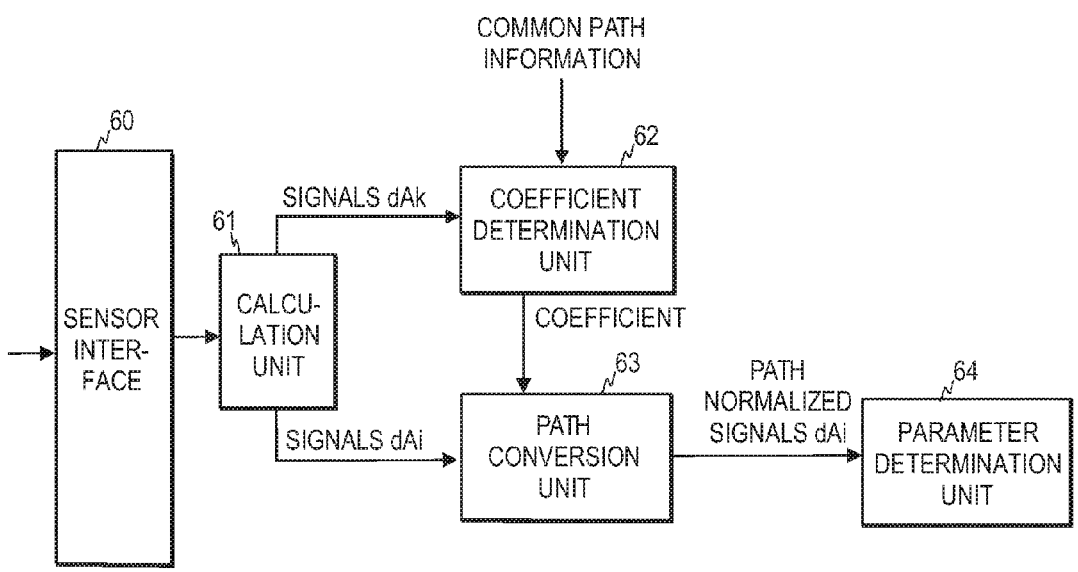
FIG. 6 illustrates the operational units carrying out the path normalization of the plethysmographic signals.

FIG. 6 illustrates the units of the control and processing unit in terms of the path normalization. It is assumed here that the in-vivo measurement signals are received from the sensor through a sensor interface 60 and that the modulation signals dAi are produced in a subsequent calculation unit 61 of the control and processing unit. In terms of the actual path normalization, the control and processing unit includes, at least in logical sense, two operational units for deriving the path normalized modulation signals from the modulation signals: a coefficient determination unit 62 adapted to determine the path normalization coefficient based on the signals dAk obtained at a common wavelength Wk and a path conversion unit 63 adapted to convert the set of input modulation signals obtained at the plurality of wavelengths from the photo detectors to a set of path normalized modulation signals. In this conversion unit, the modulation signals received through one of the photo detectors are converted to path normalized signals that can be regarded as received through the other photo detector. After the path normalization, all signals are used in a normal and known fashion by the algorithms of the control and processing unit, which is illustrated in the figure by a single parameter determination unit 64. In a real apparatus, the functionalities of the units of FIG. 6 may integrated into the $SpO_2$ or hemoglobin algorithm(s), and therefore the units of FIG. 6 may exist in the apparatus only in logical sense. It is also possible that units 61-63 are in the sensor, i.e. that the control and processing unit obtains path normalized signals from the sensor.

The above configuration allows a simple sensor assembly, since the photo detectors may be mounted in the sensor without a need to design the mechanical structure of the sensor so that the optical paths are substantially the same for the detectors. A simple mechanical structure translates to lower manufacturing and end-user costs. Furthermore, the configuration allows several types of measurements to be carried out with one sensor or with a set of sensors. One sensor may also be provided with more than two photo detectors if two spectrally adjacent detectors operate in the above-described manner for one measurement. For example, four detectors may be used if signals from detectors 1 and 2 may be used for one measurement and signals from detectors 3 and 4 for another measurement. In this case, signals from detectors 1 and 2 are normalized to the optical path of detector 1 or 2 for the first measurement and signals from detectors 3 and 4 to the optical path of detector 3 or 4 for the second measurement. Spectrally adjacent detectors may also have more than one common wavelength. Since all photo detectors may be exposed to direct light beams, no detector attenuates the signal of another detector, as is the case in the sandwich design. The detectors may be arranged in an array configuration or in a two-dimensional matrix configuration. For example, four detectors may form a 2×2 detector matrix.

In the above examples, the light sources and the photo detectors are mounted on opposite sides of the cavity so that the light pulses emitted by the light sources travel through a body part, such as finger or ear. However, the above-described solution may also be applied to measurements, in which the light sources and the photo detectors are on the same side of the body part examined. This kind of transmitter/receiver configuration may be used, for example, in a cerebral oximeter, where light is transmitted from a first location on the scalp of a subject and received at two or more other locations spaced from the first location by different distances. The detector being closest to the transmission point receives light traversed primarily only skin and bone (scalp and skull), while the detector(s) being further away receive(s) light that also traverses brain tissue. In a brain oximeter application, the in-vivo measurement signals obtained from the detectors are processed in a different manner compared to an ordinary pulse oximeter; normally no modulation signals are produced. Nevertheless, the above-described optical path length normalization may be applied to detector output signals or to signals derived from the detector output signals.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A sensor for determining blood characteristics of a subject, the sensor being attachable to the subject and comprising:
    an emitter unit configured to emit radiation through the tissue of the subject at a plurality of measurement wavelengths;
    a detector unit comprising at least a first photo detector and at least a second photo detector that are together adapted to receive the radiation at the plurality of wavelengths and to produce in-vivo measurement signals corresponding to the plurality of measurement wavelengths, the in-vivo measurement signals being indicative of absorption caused by blood of the subject, wherein the first and second photo detectors are mounted so that the optical paths from the emitter unit to the first photo detectors is different from the optical path from the emitter unit to the second photo detector and wherein the first photo detector detects a first subset of the plurality of wavelengths and the second photo detector detects a second subset of the plurality of wavelengths such that the plurality of wavelengths are divided between the first and second photo detectors, wherein the first and second subsets include at least one common wavelength; and a path normalization unit configured to normalize the in-vivo measurement signals to one of the optical paths specific to either the first or second photo detector.

2. The sensor according to claim 1, wherein the photo detectors are mounted side by side in the sensor.

3. The sensor according to claim 2, wherein the photo detectors are arranged in an array configuration.

4. The sensor according to claim 2, wherein the photo detectors are arranged in a matrix configuration.

5. The sensor according to claim 1, wherein the first and second photo detectors have an overlapping spectral responsivity range from approximately 800 nm to approximately 1000 nm, and wherein the at least one common wavelength comprises one wavelength located within the overlapping spectral responsivity range.

6. The sensor according to claim 1, wherein the sensor comprises a silicon photodiode and an InGaAs photodiode.

7. An apparatus for determining blood characteristics of a subject, the apparatus comprising:

an interface unit configured to receive in-vivo measurement signals from at least a first photo detector and a second photo detector, wherein the in-vivo measurement signals are indicative of absorption caused by blood of a subject and wherein the first photo detector is adapted to receive optical signals from a first optical path specific to the first detector and the second photo detector is adapted to receive optical signals from a second optical path specific to the second detector; and a path normalization unit configured to normalize the in-vivo measurement signals received from the first and second photo detectors to the optical path specific to either one of the first and second photo detectors based on a measurement at a common wavelength.

8. The apparatus according to claim 7, wherein the path normalization unit is configured to derive modulation signals from the in-vivo measurement signals, wherein each modulation signal represents a ratio of AC and DC signal components at a specific wavelength;

determine a ratio of two modulation signals obtained at the common wavelength detected by both the first and second photo detectors;

select a set of modulation signals; and multiply the selected modulation signals by the ratio.

9. The apparatus according to claim 7, further comprising a sensor unit attachable to the subject, the sensor unit comprising:

an emitter unit configured to emit radiation through the tissue of the subject at a plurality of measurement wavelengths; and a detector unit comprising the first and second photo detectors, wherein the photo detectors are together adapted to receive the radiation at the plurality of wavelengths and to produce the in-vivo measurement signals, wherein the first and second photo detectors are mounted so that the first and second optical paths from the emitter unit to the photo detectors are different and wherein the plurality of wavelengths are divided between the photo detectors so that two spectrally adjacent photo detectors have at least one common wavelength.

10. A method for monitoring blood characteristics of a subject, the method comprising:

mounting multiple photo detectors in a sensor arrangement so that optical paths from an emitter unit to the photo detectors are different;

providing the emitter unit with a plurality of measurement wavelengths;

acquiring in-vivo measurement signals at the plurality of measurement wavelengths, the in-vivo measurement signals being indicative of absorption caused by blood of a subject;

determining a path normalization coefficient based on different in-vivo measurement signals obtained respectively from different photo detectors at a wavelength common to the different photo detectors;

applying the path normalization coefficient to selected in-vivo measurement signals, thereby to obtain path normalized in-vivo measurement signals; and employing the path normalized in-vivo measurement signals for determining blood characteristics of the subject.

11. The method according to claim 10, wherein the determining includes deriving in-vivo modulation signals from the in-vivo measurement signals, wherein each in-vivo modulation signal represents a ratio of AC and DC signal components at a specific wavelength;

the applying includes applying the path normalization coefficient to selected in-vivo modulation signals, thereby to obtain path normalized in-vivo modulation signals; and the employing includes employing the path normalized in-vivo modulation signals for determining the blood characteristics.

* * * * *